US009301966B2

(12) United States Patent
Berg

(10) Patent No.: US 9,301,966 B2
(45) Date of Patent: Apr. 5, 2016

(54) NUTRITIONAL COMPOSITIONS CONTAINING MAGNESIUM THREONATE AND USES THEREOF

(71) Applicant: Mead Johnson Nutrition Company, Glenview, IL (US)

(72) Inventor: Brian Berg, Evansville, IN (US)

(73) Assignee: Mead Johnson Nutrition Company, Glenview, IL (US)

(*) Notice: Subject to any disclaimer, the term of this patent is extended or adjusted under 35 U.S.C. 154(b) by 90 days.

(21) Appl. No.: 13/739,813

(22) Filed: Jan. 11, 2013

(65) Prior Publication Data

US 2014/0200176 A1    Jul. 17, 2014

(51) Int. Cl.

| | |
|---|---|
| *A61K 9/00* | (2006.01) |
| *A61K 31/70* | (2006.01) |
| *A61K 31/191* | (2006.01) |
| *A61K 31/20* | (2006.01) |
| *A61K 31/202* | (2006.01) |
| *A23L 1/304* | (2006.01) |
| *A23L 1/29* | (2006.01) |
| *A61K 31/198* | (2006.01) |
| *A61K 33/06* | (2006.01) |
| *A61K 45/06* | (2006.01) |
| *A61K 35/20* | (2006.01) |
| *A61K 35/741* | (2015.01) |
| *A61K 35/00* | (2006.01) |

(52) U.S. Cl.
CPC ............... *A61K 31/70* (2013.01); *A23L 1/296* (2013.01); *A23L 1/304* (2013.01); *A61K 31/191* (2013.01); *A61K 31/198* (2013.01); *A61K 31/20* (2013.01); *A61K 31/202* (2013.01); *A61K 33/06* (2013.01); *A61K 35/20* (2013.01); *A61K 35/741* (2013.01); *A61K 45/06* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 8,377,473 B2* | 2/2013 | Liu et al. ................. | 424/468 |
| 2011/0118204 A1* | 5/2011 | Frauchiger .............. | A23L 1/296 514/47 |
| 2013/0095204 A1* | 4/2013 | Jouni et al. .............. | 426/2 |

FOREIGN PATENT DOCUMENTS

| | | | | |
|---|---|---|---|---|
| EP | 2143340 | 1/2010 | | |
| WO | 2008116226 | 9/2008 | | |
| WO | WO 2010/047581 A1 * | 4/2010 | ............. | A23L 1/29 |
| WO | WO 2012/125020 A1 * | 9/2012 | ............. | A61K 9/00 |

OTHER PUBLICATIONS

Product Details for Magtein; accessed May 14, 2013 from http://www.sourcenaturals.com/products/print'GP2423.*
FAO (Food and Agriculture Organization fo the United Nations "Human Vitamin and Mineral Requirements—Chapter 14. Magnesium" (Oct. 15, 2012) http://web.archive.org/web/20121015142116/http://www.fao.org/docrep/004/Y2809E/y2809e0k.htm; accessed May 18, 2013).*
Table 1, http://www.nal.usda.gov/wicworks/Topics/FG/Chapter1_NutritionalNeeds.pdf, (year 2000 Dietary Reference Intakes) downloaded on Dec. 6, 2013).*
FAO (Food and Agriculture Organization fo the United Nations "Human Vitamin and Mineral Requirements—Chapter 14. Magnesium" (Oct. 15, 2012) downloaded from http://web.archive.org/web/20121015142116/http://www.fao.org/docrep/OO4/Y2809E/y2809eOk.htm; accessed May 18, 2013).*
Product Details for Magtein; accessed May 14, 2013 from http://www.sourcenaturals.com/products/print/GP2423/.*
Weights of Sprague Dawley Rats provided by Charles River; http://www.criver.com/SiteCollectionDocuments/rm_rm_c_sprague_dawley_rats.pdf; downloaded May 13, 2013.*
Abumaria, N., et al., "Effects of Elevation of Brain Magnesium on Fear Conditioning, Fear Extinction, and Synaptic Plasticity in the Infralimbic Prefrontal Cortex and Lateral Amygdala," J. Neurosci, Oct. 19, 2011 31 (42):14871-14881.
AIDP Press Release, "Magtein™ Self-Affirmed as GRAS," Jul. 15, 2011.
Deutsch, J., et al., "Rapid mass spectrometric analysis for ascrobate and related organic acids in small volumes of plasma for use in pediatric subjects," J. Chromatogr. B 726 (1999) 79-84.
Ghebremeskel, K., et al., "Plasma Vitamin A and E in Preterm Babies Fed on Breast Milk or Formula Milk with or without Long-Chain Polyunsaturated Fatty Acids," Internat. J. Vit. Nutr. Res., 69 (2), 1999, 83-91.
Kim, Y., et al., "The Effects of Plasma and Brain Magnesium Concentrations on Lidocaine-Induced Seizures in the Rat," Anesth Analg 1996;83:1223-8.
Magtein Brochure.
Mercer, B., et al., "Magnesium Sulfate for Preterm Labor and Preterm Birth," Obstet Gynecol 2009;114:650-68.
McKee, J., et al., "Analysis of the brain bioavailability of peripherally administered magnesium sulfate: A study in humans with acute brain injury undergoing prolonged induced hypermagnesemia," Crit Care Med 2005 vol. 33 No. 3.
Scalabrin, D., et al., "New Prebiotic Blend of Polydextrose and Galacto-oligosaccharides Has a Bifidogenic Effect in Young Infants," JPGN, vol. 54, No. 3, Mar. 2012.
Sheng-Li, G., "Synthesis and Standard Enthalpy Formation of Magnesium L-Threonate," Acta Phys Chim Sci 2002, 18(11); 994-997.
Shokry, M., et al., "Effects of antenatal magnesium sulfate therapy on cerebral and systemic hemodynamics in preterm newborns," Acta Obstetricia et Gynecologica. 2010; 89: 801-806.
Slutsky, I., et al., "Enhancement of Learning and Memory by Elevating Brain Magnesium," Neuron 65, 165-177, Jan. 28, 2010.
Wang, H., et al., "Determination of L-threonate in human plasma and urine by high performance liquid chromatography-tandem mass spectrometry," J. Chromatogr. B 834 (2006) 155-162.
Yadomae, T., "Structure and Biological Activities of Fungal B-1, 3-Glucans," Yakugaku Zasshi 2000;120:413-431.
Bush, A., "Kalzium ist nicht alles," Neuron 28, vol. 65, Nr. 2, pp. 143-144.

* cited by examiner

*Primary Examiner* — Marcela M Cordero Garcia
*Assistant Examiner* — Mindy Newman
(74) *Attorney, Agent, or Firm* — Patterson Intellectual Property Law, P.C.; James R. Cartiglia; Bethany J. Whelan

(57) ABSTRACT

The present disclosure relates to nutritional composition(s) comprising a carbohydrate source, a protein source, a fat source and magnesium threonate. Magnesium threonate may provide neurological health benefits when consumed. The disclosure further relates to methods of promoting neurological health by providing a nutritional composition comprising magnesium threonate. Additionally, the disclosure relates to methods of promoting GI tolerance in a pediatric subject by providing a nutritional composition comprising magnesium threonate.

17 Claims, No Drawings

NUTRITIONAL COMPOSITIONS CONTAINING MAGNESIUM THREONATE AND USES THEREOF

TECHNICAL FIELD

The present disclosure relates generally to nutritional compositions comprising magnesium threonate ("MgT"). The nutritional compositions are suitable for administration to pediatric subjects. Additionally, the disclosure relates to methods of delivering magnesium to enhance brain development, cognitive functions, motor, social, stress reactivity or communication skills (nervous system health or neurological health—and harmonize throughout) of a pediatric subject by providing a nutritional composition that contains magnesium threonate. Further, the disclosure relates to methods of promoting gastrointestinal tolerance in pediatric subject by providing a nutritional composition including MgT. MgT may provide additive and/or synergistic beneficial health effects when provided to a pediatric subject.

BACKGROUND ART

The human brain and nervous system begin forming very early in prenatal life and continue to develop through adolescence. Environmental factors during this time in development can have lifelong effects on overall brain and nervous system health. Accordingly, some nutrients have become known to be increasingly important in the diets of infants, children and pregnant and lactating women because of their ability to promote early brain development and help prevent or reduce brain and nervous system injury or illness.

Magnesium, as a bivalent cation, i.e. $Mg^{2+}$, is the fourth most abundant ion in the body and serves as a co-factor for more than 300 enzymes. Magnesium is a cofactor for energy metabolism, nucleic acid synthesis and is implicated in regulation of neuronal activity. Magnesium is essential for proper functioning of the cardiovascular, neuromuscular and nervous systems.

Evidence suggests that about one third of dietary magnesium is absorbed from the gastrointestinal tract. The bulk of magnesium absorption takes place in the upper small bowel. Absorption is by means of an active process apparently related to the transport system for calcium. Ingestion of low amounts of magnesium results in increased absorption of calcium and vice versa. Therefore, one potential benefit of providing a more bioavailable form of magnesium would be that less magnesium is needed in a nutritional formulation(s), which may indirectly enhance calcium absorption which is known to be important for both brain and skeletal system development. Accordingly, providing a nutritional composition including a more bioavailable magnesium and calcium may have synergistically affect neural health and development.

Magnesium is a cofactor of all enzymes involved in phosphate transfer reactions that utilize adenosine triphosphate ("ATP") and other nucleotide triphosphates as substrates. Hypomagnesia causes increased central nervous system ("CNS") irritability, disorientation, and convulsions. Further, abnormally low concentrations of magnesium in the extracellular fluid result in increased acetylcholine release and increased muscle excitability that can produce tetany. Magnesium deficiency is also associated with oxidative neuronal cell death. Therefore, ensuring a maximal and prolonged supply of magnesium, via the use of MgT, to a developing infant or child could theoretically serve as a preventative measure to protect and conserve maximal nervous system health.

Within the brain, magnesium functions as a regulator of N-methyl-D-aspartate ("NMDA") receptors, which are critical for synaptic plasticity, and thus memory formation and consolidation (Slutsky, I., et al., *Enhancement of Learning and Memory by Elevating Brain Magnesium*. Neuron 65, 165-177: 2010). More specifically, magnesium has been shown to antagonize NMDA receptors, thus high levels of magnesium may reduce post-trauma neuronal damage and result in improved neurological outcome.

Magnesium sulfate therapy has been suggested as a neuroprotective therapy against the negative effects of preterm birth (Mercer, B., et al., *Magensium Sulfate for Preterm Labor and Preterm* Birth. Obstetrics & Gynecology, 114:3, 650-668: 2009). However, such approaches may be limited by the relative lack of bioavailability of magnesium sulfate and other magnesium salts. Therefore MgT may be of particular importance in the preterm infant, which is known to be at high risk for neurological insults and nutritional deficiencies.

It has been shown that a 3-fold increase of magnesium sulfate intravenous infusion for 5 days in rats failed to increase brain concentrations of magnesium (Kim et al., *The effects of plasma and brain magnesium concentrations on lidocaine-induced seizures in the rat*. Anesthesia & Analgesia. 1996 83:1223-1228). In adult humans, a 100%-300% increase in blood magnesium corresponded only to a 10-19% elevation in corresponding cerebrospinal fluid levels of magnesium (McKee, J. A., et al., *Analysis of the brain bioavailability of peripherally administered magnesium sulfate: A study in human with acute brain injury undergoing prolonged induced hypermagnesemia*. Critical Care Medicine. 2005 33:661-666). Therefore it has been historically difficult to modulate brain magnesium through supplementation.

It is now proposed that MgT may have an even more significant impact on nervous system health when delivered early in life when all of the fundamental aspects of the nervous system are being built to support functions required later in life. Therefore pediatric subjects who consume nutritional products that comprise magnesium sources other than MgT may not be obtaining optimum nutrition essential for brain and nervous system development.

Accordingly, it would be beneficial to provide a nutritional composition that contains MgT. More specifically, it would be beneficial to provide pediatric nutritional compositions comprising MgT since brain and nervous system growth and development are critical during the first years of life. Additionally, it is beneficial to provide a method of promoting neurological health and GI tolerance in a pediatric subject by providing a nutritional composition comprising MgT.

BRIEF SUMMARY

Briefly, the present disclosure is directed, in an embodiment, to a nutritional composition that contains a carbohydrate source, a protein source, a fat source and MgT.

In certain embodiments the nutritional composition may optionally contain β-glucan, at least one probiotic, at least one prebiotic, a source of long chain polyunsaturated fatty acids ("LCPUFA"), for example docosahexaenoic acid ("DHA") or arachidonic acid ("ARA"), a source of iron, and mixtures of one or more thereof.

Additionally, the disclosure is directed to a method of promoting neurological health in a pediatric subject by providing a nutritional composition comprising MgT. In other embodiments, the disclosure relates to methods for promoting GI tolerance in a pediatric subject by providing a nutritional composition comprising MgT.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth herein below. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

The present disclosure relates generally to nutritional compositions comprising a carbohydrate source, a protein source, a fat source and MgT. Additionally, the disclosure relates to methods of promoting neurological health by providing a nutritional composition comprising MgT. In some embodiments, the nutritional compositions described herein may be provided to a pediatric subject to promote GI tolerance of nutritional compositions.

"Nutritional composition" means a substance or formulation that satisfies at least a portion of a subject's nutrient requirements. The terms "nutritional(s)", "nutritional formula (s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or fullterm) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, and preterm infants. "Preterm" means an infant born before the end of the 37th week of gestation. "Full term" means an infant born after the end of the 37th week of gestation.

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As used herein "magnesium threonate" or "MgT" includes, but is not limited to, the complexed salt form of MgT as MgT2. In other embodiments, magnesium and threonate may include other magnesium salts and/or threonate salts. When magnesium is not in the form of magnesium threonate but another magnesium salt, the other magnesium salt may be any suitable inorganic or organic magnesium salt. Similarly, when threonate is not in the form of magnesium threonate, it may be in the form of another threonate salt comprising a cation other than Mg. Threonate may comprise one or more of a threonate salt or threonate precursor. Generally, the present disclosure uses the term "threonate" to comprise threonate and precursors thereof, including salts, acids, esters and lactones, by way of example. Examples of threonate precursors include, but are not limited to, a threonic acid, an ester derivative of threonic acid or threonate, or a lactonized threonic acid. Further, threonate as used herein may include L-threonate or a L-threonate precursor, including but not limited to, L-threonic acid, an ester derivative of L-threonic acid or L-threonate or lactonized L-threonic acid.

In some embodiments, D-threonate or precursors thereof may be included.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The present disclosure is directed to nutritional compositions containing a carbohydrate source, a protein source, a fat source, and MgT. MgT is a magnesium salt of L-threonic acid having the molecular formula Mg(C$_4$H$_7$O$_5$)$_2$ and a molecular weight of 294.5 grams per mole. See below:

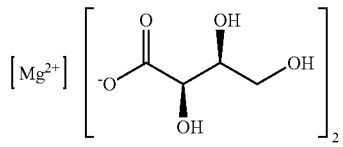

In some embodiments the nutritional composition may comprise MgT from about 4.9 mg/100 kcal to about 45 mg/100 kcal. In other embodiments, MgT is present from about 6 mg/100 kcal to about 34 mg/100 kcal. In still other embodiments, MgT is present from about 15 mg/100 kcal to about 25 mg/100 kcal.

MgT included in the nutritional composition in some embodiments may include MgT-functional equivalents, MgT-sources, MgT-metabolites and/or MgT-prerequisites, all referred to herein as MgT. Such MgT may be naturally occurring, synthetic, or developed through the genetic manipulation of organisms and/or plants, whether such source is now known or developed later.

MgT may be commercially obtained from AIDP Inc., Industry, CA, U.S.A. Other suitable sources for MgT for use in the present disclosure include, include any other resource, fortified or not, from which MgT could be obtained and used in a nutritional composition. Further, the source of MgT could be part of a complex mixture obtained by separation and purification technology known in the art aimed at the enrichment of the MgT and derivatives or precursors of MgT of such mixtures. Additionally, synthetic MgT may be obtained from any process known in the art including the procedure described in Sheng-Li, G., *Synthesis and Standard Enthalpy Formation of Magnesium L-Threonate*. Acta Phys Chim Sci 2002, 18(11); 994-997, however any other suitable procedure for the synthesis of MgT may be used.

Once the desired form of MgT is obtained, it may be incorporated into the nutritional composition(s) described herein by any method well-known in the art. In some embodiments, MgT may be added to the nutritional composition by replacing an equivalent amount of the magnesium source normally present in the nutritional composition. In some embodiments, a certain amount of a magnesium source that does not contain MgT may be substituted with MgT. In yet another embodiment, the nutritional composition may be supplemented with MgT. Further, in other embodiments, MgT may be the sole source of magnesium in the nutritional composition.

In one embodiment, where the nutritional composition is an infant formula, MgT may be added to a commercially available infant formula. For example, Enfalac, Enfamil®, Enfamil® Premature Formula, Enfamil® with Iron, Enfamil® LIPIL®, Enfamil® Premium, Enfamil® Newborn, EnfaGrow®, Lactofree®, Nutramigen®, Pregestimil®, and ProSobee®, each of which is available from Mead Johnson & Company, Evansville, Ind., U.S.A. may be supplemented with MgT, and used in the practice of the present disclosure.

The nutritional composition(s) of the present disclosure may also comprise a carbohydrate source. Carbohydrate sources can be any used in the art, e.g., lactose, glucose, fructose, corn syrup solids, maltodextrins, sucrose, starch, rice syrup solids, and the like. The amount of carbohydrate in the nutritional composition typically can vary from between about 5 g/100 kcal and about 25 g/100 kcal. In some embodiments, the amount of carbohydrate is between about 6 g/100 kcal and about 22 g/100 kcal. In other embodiments, the amount of carbohydrate is between about 12 g/100 kcal and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

The nutritional composition(s) of the disclosure may also comprise a protein source. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In one embodiment, the proteins of the nutritional composition are provided as intact proteins. In other embodiments, the proteins are provided as a combination of both intact proteins and partially hydrolyzed proteins, with a degree of hydrolysis of between about 4% and 10%. In certain other embodiments, the proteins are more completely hydrolyzed. In still other embodiments, the protein source comprises amino acids. In yet another embodiment, the protein source may be supplemented with glutamine-containing peptides.

In a particular embodiment of the nutritional composition, the whey:casein ratio of the protein source is similar to that found in human breast milk. In an embodiment, the protein source comprises from about 40% to about 80% whey protein and from about 20% to about 60% casein.

In some embodiments, the nutritional composition comprises between about 1 g and about 7 g of a protein source per 100 kcal. In other embodiments, the nutritional composition comprises between about 3.5 g and about 4.5 g of protein source per 100 kcal.

In some embodiments, the nutritional composition described herein comprises a fat source. Appropriate fat sources include, but are not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In some embodiments the nutritional composition may also include a source of LCPUFAs. In one embodiment the amount of LCPUFA in the nutritional composition is advantageously at least about 5 mg/100 kcal, and may vary from about 5 mg/100 kcal to about 100 mg/100 kcal, more preferably from about 10 mg/100 kcal to about 50 mg/100 kcal. Non-limiting examples of LCPUFAs include, but are not limited to, DHA, eicosapentaenoic acid (EPA), ARA, linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic (20:5 n-3), and docosapentaenoic (22:6 n-3).

In some embodiments, the LCPUFA included in the nutritional composition may comprise DHA. In one embodiment the amount of DHA in the nutritional composition is advantageously at least about 17 mg/100 kcal, and may vary from about 5 mg/100 kcal to about 75 mg/100 kcal, more preferably from about 10 mg/100 kcal to about 50 mg/100 kcal.

In another embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The DHA and ARA can be in natural form, provided that the remainder of the LCPUFA source does not result in any substantial deleterious effect on the infant. Alternatively, the DHA and ARA can be used in refined form.

The disclosed nutritional composition described herein can, in some embodiments, also comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., *Structure and biological activities of fungal beta-1,3-glucans*. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

In some embodiments, the β-glucan is β-1,3;1,6-glucan. In some embodiments, the β-1,3;1,6-glucan is derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

In some embodiments, the amount of β-glucan in the nutritional composition is between about 3 mg and about 17 mg per 100 kcal. In another embodiment the amount of β-glucan is between about 6 mg and about 17 mg per 100 kcal.

A source of probiotic may be present in some embodiments of the nutritional composition described herein. The term "probiotic" means a microorganism that exerts beneficial effects on the health of the host. Any probiotic known in the art may be acceptable in this embodiment. In a particular embodiment, the probiotic may be selected from any *Lactobacillus* species, *Lactobacillus rhamnosus* GG (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve*

AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included, the nutritional composition may comprise between about $1 \times 10^4$ to about $1.5 \times 10^{10}$ cfu of probiotics per 100 kcal, more preferably from about $1 \times 10^6$ to about $1 \times 10^9$ cfu of probiotics per 100 kcal.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such new source is now known or later developed.

The nutritional composition(s) of the present disclosure may, in some embodiments, contain a source of prebiotics. The term "prebiotic" as used herein refers to indigestible food ingredients which exert health benefits upon the host. Such health benefits may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides. In a preferred embodiment, the prebiotic source comprises galacto-oligosaccharide and polydextrose and mixtures thereof.

The amount of galacto-oligosaccharide in the nutritional composition may, in an embodiment, be from about 0.1 mg/100 kcal to about 1.0 mg/100 kcal. In another embodiment, the amount of galacto-oligosaccharide in the nutritional composition may be from about 0.1 mg/100 kcal to about 0.5 mg/100 kcal. The amount of polydextrose in the nutritional composition may, in an embodiment, be within the range of from about 0.1 mg/100 kcal to about 0.5 mg/100 kcal. In a particular embodiment, galacto-oligosaccharide and polydextrose are supplemented into the nutritional composition in a total amount of about at least about 0.2 mg/100 kcal and can be about 0.2 mg/100 kcal to about 1.5 mg/100 kcal. In some embodiments, the nutritional composition may comprise galactooligosaccharide and polydextrose in a total amount of from about 0.6 mg/100 kcal to about 0.8 mg/100 kcal.

The disclosed nutritional composition described herein, can, in some embodiments also comprise an effective amount of iron. The iron may comprise encapsulated iron forms, such as encapsulated ferrous fumarate or encapsulated ferrous sulfate or less reactive iron forms, such as ferric pyrophosphate or ferric orthophosphate.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In embodiments providing a nutritional composition for a child, the composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

In embodiments providing a children's nutritional product, such as a growing-up milk, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

Flavoring agents may be added to some embodiments of the nutritional compositions of the present disclosure. These flavoring agents may include, but are not limited to the following, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

In some embodiments, the nutritional composition may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

A stabilizer may be optionally included in some embodiments of the nutritional composition(s) of the present disclosure. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 1 to about 25 g/100 kcal. The amount of protein typically can vary from about 1 to about 7 g/100 kcal. The amount of carbohydrate typically can vary from about 6 to about 22 g/100 kcal.

In an embodiment, the children's nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

In some embodiments the nutritional composition is an infant formula. Infant formulas are fortified nutritional compositions for an infant. The content of an infant formula is dictated by federal regulations, which define macronutrient, vitamin, mineral, and other ingredient levels in an effort to simulate the nutritional and other properties of human breast milk. Infant formulas are designed to support overall health and development in a pediatric human subject, such as an infant or a child.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a growing-up milk or other nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition includes an enriched lipid fraction derived from milk. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 μm, more preferably in the range of 10 μm to 300 μm.

Additionally, in some embodiments of the method described herein, the nutritional composition provided is an infant formula comprising MgT.

Further, in some embodiments the disclosure is directed to a method for promoting brain and nervous system development in a pediatric subject by providing a nutritional composition comprising a carbohydrate source, a protein source, a fat source and MgT.

In other embodiments, the disclosure is directed to a method for promoting GI tolerance in a pediatric subject by proving a nutritional composition comprising MgT as the magnesium component.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

Formulation examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

FORMULATION EXAMPLES

The following formulation examples provide a nutritional composition according to the present disclosure and describes the amount of each ingredient to be included per 100 kcal serving or per 100 grams of nutritional composition.

TABLE 1

Preterm infant nutritional composition comprising MgT

| Nutrient | per 100 kcal |
|---|---|
| Protein (g) | 3 |
| Fat (g) | 5.1 |
| Carbohydrates (g) | 11 |
| MgT (mg) | 9 |
| DHA (mg) | 17 |
| ARA (mg) | 34 |
| Vitamin A (IU) | 1,250 |
| Vitamin D (IU) | 240 |
| Vitamin E (IU) | 6.3 |
| Vitamin K (mcg) | 8 |
| Thiamin (mcg) | 200 |
| Riboflavin (mcg) | 300 |
| Vitamin B6 (mcg) | 150 |
| Vitamin B12 (mcg) | 0.25 |
| Niacin (mcg) | 4,000 |
| Folic acid (mcg) | 40 |
| Panthothenic acid (mcg) | 1,200 |
| Biotin (mcg) | 4 |
| Vitamin C (mg) | 20 |
| Choline (mg) | 20 |
| Calcium (mg) | 165 |
| Phosphorus (mg) | 83 |
| Sodium (mg) | 58 |
| Potassium (mg) | 98 |
| Chloride (mg) | 90 |
| Iodine (mcg) | 25 |
| Iron (mg) | 1.8 |
| Zinc (mg) | 1.5 |
| Manganese (mcg) | 6.3 |
| Copper (mcg) | 120 |
| Selenium (mcg) | 2.8 |
| Chromium (mcg) | 0.2 |
| Molybdenum (mcg) | 0.4 |
| Inositol (mg) | 44 |
| Carnitine (mg) | 2.4 |
| Taurine (mg) | 6 |
| Adenosine monophosphate (mg) | 0.5 |
| Cytidine monophosphate (mg) | 2.5 |
| Guanosine monophosphate (mg) | 0.3 |
| Uridine monophosphate (mg) | 0.9 |

TABLE 2

Term infant nutritional composition comprising MgT

| Nutrient | per 100 kcal |
|---|---|
| Protein (g) | 2.1 |
| Fat (g) | 5.3 |
| Carbohydrates (g) | 11.2 |
| Prebiotic (g) | 0.6 |
| Beta glucan (mg) | 10 |
| Probiotic (cfu) | $6.5 \times 10^7$ |
| MgT (mg) | 8 |
| DHA (mg) | 17 |
| ARA (mg) | 34 |
| Vitamin A (IU) | 300 |
| Vitamin D (IU) | 75 |
| Vitamin E (IU) | 2 |
| Vitamin K (mcg) | 9 |
| Thiamin (mcg) | 80 |
| Riboflavin (mcg) | 140 |
| Vitamin B6 (mcg) | 60 |
| Vitamin B12 (mcg) | 0.3 |
| Niacin (mcg) | 1,000 |
| Folic acid (mcg) | 16 |
| Panthothenic acid (mcg) | 500 |
| Biotin (mcg) | 3 |
| Vitamin C (mg) | 12 |
| Choline (mg) | 24 |
| Calcium (mg) | 78 |
| Phosphorus (mg) | 43 |
| Sodium (mg) | 27 |
| Potassium (mg) | 108 |
| Chloride (mg) | 63 |
| Iodine (mcg) | 15 |
| Iron (mg) | 1.8 |
| Zinc (mg) | 1 |
| Manganese (mcg) | 15 |
| Copper (mcg) | 75 |
| Selenium (mcg) | 2.8 |
| Inositol (mg) | 6 |
| Carnitine (mg) | 2 |
| Taurine (mg) | 6 |
| Total nucleotides (mg) | 4.2 |

TABLE 3

Growing up milk nutritional composition comprising MgT

| Nutrient | Per 100 g |
|---|---|
| Protein (g) | 16.5 |
| Fat (g) | 11.5 |
| Carbohydrates (g) | 65 |
| Prebiotic (g) | 3 |
| MgT (mg) | 45 |

TABLE 3-continued

Growing up milk nutritional composition comprising MgT

| Nutrient | Per 100 g |
|---|---|
| DHA (mg) | 35 |
| Vitamin A (IU) | 1,250 |
| Vitamin D (IU) | 150 |
| Vitamin E (IU) | 7.3 |
| Vitamin K (mcg) | 38 |
| Thiamin (mcg) | 460 |
| Riboflavin (mcg) | 750 |
| Vitamin B6 (mcg) | 300 |
| Vitamin B12 (mcg) | 1.13 |
| Niacin (mcg) | 5,000 |
| Folic acid (mcg) | 80 |
| Panthothenic acid (mcg) | 2,500 |
| Biotin (mcg) | 8.3 |
| Vitamin C (mg) | 30 |
| Choline (mg) | 100 |
| Calcium (mg) | 750 |
| Phosphorus (mg) | 420 |
| Sodium (mg) | 200 |
| Potassium (mg) | 700 |
| Chloride (mg) | 480 |
| Iodine (mcg) | 75 |
| Iron (mg) | 7.8 |
| Zinc (mg) | 3.8 |
| Manganese (mcg) | 270 |
| Copper (mcg) | 370 |
| Taurine (mg) | 35 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the use of the nutritional composition have been exemplified, other uses are contemplated. Therefore, the spirit and scope of the appended claims should not be limited to the description of the versions contained therein.

What is claimed is:

1. A nutritional composition comprising per 100 kcal:
   (i) between about 6 g and about 22 g of a carbohydrate source,
   (ii) between about 1 g and about 7 g of a protein source,
   (iii) between about 1 g and about 10.3 g of a fat source, and
   (iv) about 4.9 mg/100 kcal to about 45 mg/100 kcal of magnesium threonate.

2. The nutritional composition of claim 1, further comprising a prebiotic.

3. The nutritional composition of claim 2, wherein the prebiotic is selected from the group consisting of polydextrose and galacto-oligosaccharide.

4. The nutritional composition of claim 1, further comprising DHA from about 5 mg to about 75 mg.

5. The nutritional composition of claim 1, further comprising a probiotic from about $1 \times 10^4$ cfu to about $1.5 \times 10^{10}$ cfu.

6. The nutritional composition of claim 1, wherein the nutritional composition is an infant formula.

7. A method of promoting GI tolerance in a pediatric subject by providing a nutritional composition comprising between about 6 g and about 22 g of a carbohydrate source, between about 1 g and about 7 g of a protein source, between about 1 g and about 10.3 g of a fat source, and between about 4.9 mg and about 45 mg of magnesium threonate per 100 kcal of nutritional composition to a pediatric subject, wherein the occurrence of oxidative neuronal cell death is reduced.

8. The method of claim 7, wherein the nutritional composition comprises per 100 kcal:
   (i) between about 6 g and about 22 g of a carbohydrate source;
   (ii) between about 1 g and about 7 g of a protein source;
   (iii) between about 1 g and about 10.3 g of a fat source;
   (iv) between about 0.1 mg and about 1 mg of polydextrose; and
   (v) between about 0.1 mg and about 1 mg of galacto-oligosaccharide.

9. The method of claim 7, wherein the nutritional composition comprises magnesium threonate from about 6 mg/100 kcal to about 26 mg/100 kcal.

10. The method of claim 7, wherein the nutritional composition comprises magnesium threonate from about 15 mg/100 kcal to about 25 mg/100 kcal.

11. The method of claim 7, wherein the nutritional composition further comprises DHA.

12. The method of claim 7, wherein the nutritional composition is an infant formula.

13. A method of promoting neurological health in a pediatric subject by providing to a pediatric subject a nutritional composition comprising between about 6 g and about 22 g of a carbohydrate source, between about 1 g and about 7 g of a protein source, between about 1 g and about 10.3 g of a fat source, and between about 4.9 mg and about 45 mg magnesium threonate per 100 kcal, wherein the occurrence of oxidative neuronal cell death is reduced.

14. The method of claim 13, wherein the nutritional composition comprises magnesium threonate from about 6 mg/100 kcal to about 26 mg/100 kcal.

15. The method of claim 13, wherein the nutritional composition comprises magnesium threonate from about 15 mg/100 kcal to about 25 mg/100 kcal.

16. The method of claim 13, wherein the nutritional composition further comprises DHA.

17. The method of claim 13, wherein the nutritional composition is an infant formula.

* * * * *